United States Patent
Yuan et al.

(10) Patent No.: US 10,758,462 B2
(45) Date of Patent: *Sep. 1, 2020

(54) ORAL CARE COMPOSITION

(71) Applicant: COLGATE-PALMOLIVE COMPANY, New York, NY (US)

(72) Inventors: Shaotang Yuan, East Brunswick, NJ (US); Guofeng Xu, Plainsboro, NJ (US); LaTonya Kilpatrick-Liverman, Princeton, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/352,614

(22) Filed: Nov. 16, 2016

(65) Prior Publication Data

US 2018/0133129 A1  May 17, 2018

(51) Int. Cl.
*A61K 8/23* (2006.01)
*A61Q 11/00* (2006.01)
*A61K 8/86* (2006.01)
*A61K 8/81* (2006.01)

(52) U.S. Cl.
CPC .............. *A61K 8/23* (2013.01); *A61K 8/8176* (2013.01); *A61K 8/86* (2013.01); *A61Q 11/00* (2013.01); *A61K 2800/48* (2013.01)

(58) Field of Classification Search
CPC ....................................................... A61K 7/20
USPC .......................................................... 424/53
See application file for complete search history.

(56) References Cited

U.S. PATENT DOCUMENTS

| | | | | |
|---|---|---|---|---|
| 3,518,343 | A * | 6/1970 | Palermo | A61K 8/02 106/38.22 |
| 4,971,782 | A * | 11/1990 | Rudy | A61K 8/11 424/53 |
| 6,264,703 | B1 | 7/2001 | Coope | |
| 6,274,122 | B1 | 8/2001 | McLaughlin | |
| 7,018,622 | B2 * | 3/2006 | Goodhart | A61C 19/063 424/401 |
| 2006/0078512 | A1 | 4/2006 | McLaughlin | |
| 2006/0099154 | A1 * | 5/2006 | Kahwaty | A61K 8/19 424/53 |
| 2007/0138674 | A1 | 6/2007 | Anastasiou et al. | |
| 2007/0270581 | A1 * | 11/2007 | Jungles | A61K 9/2018 536/26.4 |
| 2008/0050398 | A1 | 2/2008 | Bockmuehl et al. | |
| 2008/0260660 | A1 | 10/2008 | Engelbrecht et al. | |
| 2009/0186081 | A1 * | 7/2009 | Holm | A61K 9/2009 424/464 |
| 2010/0135921 | A1 * | 6/2010 | Hughes | A61K 8/25 424/49 |
| 2012/0282192 | A1 * | 11/2012 | Miller | A61K 8/22 424/52 |
| 2014/0377194 | A1 | 12/2014 | Strand et al. | |
| 2016/0296433 | A1 | 10/2016 | Chen et al. | |
| 2017/0014320 | A1 | 1/2017 | Chen et al. | |

FOREIGN PATENT DOCUMENTS

| | | |
|---|---|---|
| EP | 0157464 | 10/1985 |
| EP | 0723579 | 5/2007 |
| GB | 2290234 | 12/1995 |
| WO | WO 2000/009079 A1 | 2/2000 |
| WO | WO 2004/000372 | 12/2003 |
| WO | WO 2015/084295 | 6/2015 |
| WO | WO 2015/084296 | 6/2015 |

OTHER PUBLICATIONS

International Search Report and Written Opinion in International Application No. PCT/US2016/062120, dated Jan. 11, 2017.

\* cited by examiner

*Primary Examiner* — Walter E Webb (57) ABSTRACT

An oral care composition, including from about 0.01% to about 40% peroxysulfate whitening agent and from about 1% to about 99% non-aqueous dispersant.

9 Claims, 1 Drawing Sheet

ORAL CARE COMPOSITION

BACKGROUND

Oral care products with teeth whitening attributes use a variety of active ingredients to remove stains or whiten teeth. The most commonly used whitening active ingredients are peroxides, such as hydrogen peroxide. However, in high concentrations, hydrogen peroxide can be irritating to the teeth and gums and, in addition, hydrogen peroxide is an unstable molecule that is prone to decomposition, especially in aqueous environments.

Alternative oxidizing agents, such as peroxysulfuric acid or peroxysulfates, have been used as stain removing agents. However, because of their high reactivity and instability in aqueous solutions, these oxidizing agents have seen limited use in oral care compositions.

Accordingly, there is a desire for oral care composition using non-hydrogen peroxide oxidizing agents, such as peroxysulfuric acid or peroxysulfates, which are stable.

BRIEF SUMMARY

This summary is intended merely to introduce a simplified summary of some aspects of one or more embodiments of the present disclosure. Further areas of applicability of the present invention will become apparent from the detailed description provided hereinafter. This summary is not an extensive overview, nor is it intended to identify key or critical elements of the present teachings, nor to delineate the scope of the disclosure. Rather, its purpose is merely to present one or more concepts in simplified form as a prelude to the detailed description below.

The foregoing and/or other aspects and utilities embodied in the present disclosure may be achieved by providing an oral care composition, including from about 0.01% to about 40% peroxysulfate whitening agent, based on a total weight of the oral care composition; and from about 1% to about 99% non-aqueous dispersant, based on the total weight of the oral care composition.

In another embodiment, the peroxysulfate whitening agent includes potassium peroxymonosulfate.

In another embodiment, the non-aqueous dispersant includes a liquid or paste poloxamer.

In another embodiment, the liquid poloxamer includes polyoxyethylene-polyoxypropylene glycol.

In another embodiment, the non-aqueous dispersant includes polyethylene glycol.

In another embodiment, the non-aqueous dispersant includes polyethylene/polypropylene glycol copolymers.

In another embodiment, the oral care composition further includes from about 1% to about 60% structural builder, based on the total weight of the oral care composition.

In another embodiment, the structural builder includes a cross-linked polymer.

In another embodiment, the structural builder includes a cross-linked polyvinylpyrrolidone (PVP).

In another embodiment, the oral care composition includes from about 0.01% to about 40% MPS as the peroxysulfate whitening agent; from about 1% to about 99% liquid poloxamer as the non-aqueous dispersant; and from about 1% to about 60% PVP as the structural builder.

In another embodiment, the liquid poloxamer includes polyoxyethylene-polyoxypropylene glycol.

In another embodiment, a viscosity of the oral care composition is from about 50000 to about 500000 cPs.

In another embodiment, an active oxygen content of the oral care composition is greater than about 70% of an initial active oxygen content of the oral care composition after 8 weeks of aging at 40° C.

In another embodiment, an active oxygen content of the oral care composition is greater than about 70% of an initial active oxygen content of the oral care composition after 13 weeks of aging at 40° C.

In another embodiment, the oral care further includes at least one of a surfactant, a thickening agent, an antioxidant, a flavoring, a sweetener, a pH modifiers, an abrasive, an anticalculus agent, a source of fluoride ions, a stannous ion source, a colorant, and a dye or pigment.

In another embodiment, all ingredients are orally acceptable, and the oral care composition includes from about 0.2 to about 10% peroxysulfate whitening agent; from about 10% to 40% structural builder; and from about 20% to about 60% of a non-aqueous or low water dispersant, wherein the structural builder includes a cross-linked polyvinylpyrrolidone (PVP), wherein the non-aqueous or low water dispersant includes polyoxyethylene-polyoxypropylene glycol, and wherein a moisture range of the oral care composition is about 5% or less.

In another embodiment, the oral care composition does not include a hydrogen peroxide compound.

In another embodiment, the oral care composition is a dentifrice.

The foregoing and/or other aspects and utilities embodied in the present disclosure may also be achieved by providing a method of whitening a tooth surface, including applying an oral care composition to the tooth surface; and activating the oral care composition by exposing the oral care composition to water or saliva; and wherein the oral care composition includes from about 0.01% to about 40% peroxysulfate whitening agent, based on a total weight of the oral care composition; and from about 1% to about 99% non-aqueous dispersant, based on the total weight of the oral care composition.

In another embodiment, a viscosity of the oral care composition is from about 50,000 cPs to about 500,000 cPs, and the oral care composition includes from about 0.01% to about 40% MPS as the peroxysulfate whitening agent; from about 1% to about 99% liquid poloxamer as the non-aqueous dispersant; and from about 1% to about 60% PVP as a structural builder.

The foregoing and/or other aspects and utilities embodied in the present disclosure may be achieved by providing an oral care composition substantially as hereinbefore described, with reference to the examples and excluding, if any, comparative examples.

BRIEF DESCRIPTION OF THE DRAWINGS

The accompanying drawings, which are incorporated in and constitute a part of this specification, illustrate embodiments of the present teachings. These and/or other aspects and advantages in the embodiments of the disclosure will become apparent and more readily appreciated from the following description of the various embodiments, taken in conjunction with the accompanying drawings of which.

These drawings/figures are intended to be explanatory and not restrictive.

DETAILED DESCRIPTION

Reference will now be made in detail to the various embodiments in the present disclosure, examples of which are illustrated in the accompanying drawings and figures. The embodiments are described below to provide a more complete understanding of the components, processes, compositions, and apparatuses disclosed herein. Any examples given are intended to be illustrative, and not restrictive. However, it will be apparent to one of ordinary skill in the art that the invention may be practiced without these specific details. In other instances, well-known methods, procedures, and components have not been described in detail so as not to unnecessarily obscure aspects of the embodiments.

Throughout the specification and claims, the following terms take the meanings explicitly associated herein, unless the context clearly dictates otherwise. The phrases "in some embodiments" and "in an embodiment" as used herein do not necessarily refer to the same embodiment(s), though they may. Furthermore, the phrases "in another embodiment" and "in some other embodiments" as used herein do not necessarily refer to a different embodiment, although they may. As described below, various embodiments may be readily combined, without departing from the scope or spirit of the present disclosure.

As used herein, the term "or" is an inclusive operator, and is equivalent to the term "and/or," unless the context clearly dictates otherwise. The term "based on" is not exclusive and allows for being based on additional factors not described, unless the context clearly dictates otherwise. In the specification, the recitation of "at least one of A, B, and C," includes embodiments containing A, B, or C, multiple examples of A, B, or C, or combinations of A/B, A/C, B/C, A/B/B/ BB/C, AB/C, etc. In addition, throughout the specification, the meaning of "a," "an," and "the" include plural references. The meaning of "in" includes "in" and "on."

It will also be understood that, although the terms first, second, etc. may be used herein to describe various elements, these elements should not be limited by these terms. These terms are only used to distinguish one element from another. For example, a first object, component, or step could be termed a second object, component, or step, and, similarly, a second object, component, or step could be termed a first object, component, or step, without departing from the scope of the invention. The first object, component, or step, and the second object, component, or step, are both, objects, component, or steps, respectively, but they are not to be considered the same object, component, or step. It will be further understood that the terms "includes," "including," "comprises" and/or "comprising," when used in this specification, specify the presence of stated features, steps, operations, elements, and/or components, but do not preclude the presence or addition of one or more other features, steps, operations, elements, components, and/or groups thereof. Further, as used herein, the term "if" may be construed to mean "when" or "upon" or "in response to determining" or "in response to detecting," depending on the context.

All physical properties that are defined hereinafter are measured at 20° to 25° Celsius unless otherwise specified.

When referring to any numerical range of values herein, such ranges are understood to include each and every number and/or fraction between the stated range minimum and maximum, as well as the endpoints. For example, a range of 0.5-6% would expressly include all intermediate values of, for example, 0.6%, 0.7%, and 0.9%, all the way up to and including 5.95%, 5.97%, and 5.99%, among many others. The same applies to each other numerical property and/or elemental range set forth herein, unless the context clearly dictates otherwise.

Unless otherwise specified, all percentages and amounts expressed herein and elsewhere in the specification should be understood to refer to percentages by weight. The amounts given are based on the active weight of the material.

Additionally, all numerical values are "about" or "approximately" the indicated value, and take into account experimental error and variations that would be expected by a person having ordinary skill in the art. It should be appreciated that all numerical values and ranges disclosed herein are approximate valves and ranges, whether "about" is used in conjunction therewith.

With regard to procedures, methods, techniques, and workflows that are in accordance with some embodiments, some operations in the procedures, methods, techniques, and workflows disclosed herein may be combined and/or the order of some operations may be changed.

The present inventors have surprisingly discovered a stable oral care composition that uses peroxysulfuric acid or peroxysulfates as a teeth whitening agent.

In one embodiment, the oral care composition includes the acids and salts of peroxy derivatives compounds selected from the main group 6A, 5A, 4A and 7A elements, such as sulfur, phosphorous, carbon, chlorine, bromine and iodine. For example, in one embodiment, the oral care composition may use peroxydisultate, peroxydiphosphate and peroxydicarboate as teeth whitening agents. In another embodiment, the oral care composition includes potassium peroxymonosulfate ("MPS") as the teeth whitening agent.

In one embodiment, the oral care composition includes a whitening agent and a dispersant. In another embodiment, the oral care composition includes a whitening agent, a dispersant, and a structural builder.

In some embodiments, the oral care composition may include additional ingredients common to oral care compositions, such as thickeners, flavoring agents, tartar control agents, surfactants, sweeteners, humectants, colorants, dyes, and pigments.

All ingredients used in the compositions described herein should be orally acceptable. "Orally acceptable" means an ingredient which is present in the composition as described in an amount and form which does not render the composition unsafe, unpalatable, or otherwise unsuitable for use in the oral cavity.

As described above, the oral care composition includes one or more whitening agent. As used herein, a "whitening agent" is a material which effects whitening of a tooth surface to which it is applied. For example, in some embodiments, the whitening agent is an oxidizing agent. In its broadest sense, "oxidizing agent" is intended to include those compounds which can accept an electron from another molecule in the environment of the oral cavity without having a deleterious or unacceptably harmful effect on the oral cavity in normal and accepted use.

In one embodiment, the whitening agent can be any suitable salt of peroxysulfuric acid, including peroxymonosulfates and peroxydisulfates, such as potassium peroxymonosulfate and sodium peroxymonosulfate, or a mixture of such salts. An example of a particularly useful whitening agent is a triple salt mixture comprising potassium hydrogen peroxymonosulfate, potassium hydrogen sulfate, and potassium sulfate. Optionally, such a mixture may further include potassium peroxydilsulfate. An example of such a commercially available mixture is "OXONE", which is the trade name of a mixture sold by DuPont, headquartered in Wilmington, Del. Another example is CAROAT, available from United Initiators, headquartered in Pullach, Germany. OXONE consists of 43% potassium hydrogen peroxymonosulfate, 23% potassium hydrogen sulfate, 29% potassium sulfate, 3% potassium peroxidisulfate, and 2% magnesium carbonate. Mixtures of these potassium reagents are usually available as a powder or solid which, when dissolved in water, typically forms a highly acidic solution (e.g., pH 1-4) which is fairly stable on storage. For example, a 1-3% solution of OXONE has a pH of 2.0-2.3. Above pH 6, however, these mixtures are strong oxidizing agents which readily decompose to release reactive oxygen species. Many sources use the terms "potassium hydrogen peroxymonosulfate" or "potassium peroxymonosulfate" to refer to the above triple salt mixture that comprises OXONE ($2KHSO_5$—$KHSO_4$—$K_2SO_4$). As used herein, however, the terms "potassium hydrogen peroxymonosulfate," "potassium peroxymonosulfate," and "MPS" refer to the individual chemical species with the formula $KHSO_5$.

In some embodiments, the whitening agent is a non-hydrogen peroxide whitening agent. In some embodiments, the oral care composition does not include hydrogen peroxide.

In various embodiments, one or more additional whitening agents may be present to enhance the effectiveness of the peroxysulfate whitening agent. Such additional whitening agents may include peroxides and hydroperoxides, such as hydrogen peroxide, peroxides of alkali and alkaline earth metals, organic peroxy compounds, peroxy acids, salts thereof, and mixtures thereof. Peroxides of alkali and alkaline earth metals include lithium peroxide, potassium peroxide, sodium peroxide, magnesium peroxide, calcium peroxide, barium peroxide, and mixtures thereof. Organic peroxy compounds include urea peroxide, carbamide peroxide (also known as urea hydrogen peroxide), glyceryl hydrogen peroxide, alkyl hydrogen peroxides, dialkyl peroxides, alkyl peroxy acids, peroxy esters, diacyl peroxides, benzoyl peroxide, and monoperoxyphthalate, and mixtures thereof. Peroxy acids and their salts include organic peroxy acids such as alkyl peroxy acids, and monoperoxyphthalate and mixtures thereof, as well as inorganic peroxy acid salts such as percarbonate, perphosphate, perborate and persilicate salts of alkali and alkaline earth metals such as lithium, potassium, sodium, magnesium, calcium and barium, and mixtures thereof. In some embodiments a non-peroxide whitening agent may be provided. Whitening agents among those useful herein include non-peroxy compounds, such as chlorine dioxide, chlorites and hypochlorites. Chlorites and hypochlorites include those of alkali and alkaline earth metals such as lithium, potassium, sodium, magnesium, calcium and barium. Non-peroxide whitening agents also include colorants, such as titanium dioxide and hydroxyapatite.

In one embodiment, the whitening agent has a stronger whitening efficacy than hydrogen peroxide. In another embodiment, the whitening agent has a stronger whitening efficacy than hydrogen peroxide even at the same level of active oxygen.

In one embodiment, the oral care composition includes one or more whitening agents. For example, the oral care composition may include from about 0.01% to about 40% peroxysulfate whitening agent based on the total weight of the oral care composition. In another embodiment, the oral care composition includes from about 0.1% to about 20% peroxysulfate whitening agent. In yet another embodiment, the oral care composition includes from about 0.2% to about 10% peroxysulfate whitening agent. For example, in one embodiment, the oral care composition includes from about 0.01% to about 40% MPS, from about 0.1% to about 20% MPS, or from about 0.2% to about 10% MPS. In one embodiment, the oral care composition includes about 0.5% MPS based on the total weight of the oral care composition.

According to embodiments of the present disclosure, the oral care composition includes one or more dispersants.

In one embodiment, the whitening agent is initially in a powdered or solid form and is dispersed by the dispersant to form the oral care composition.

While MPS is somewhat unstable in aqueous solutions at acidic pH, as revealed by the present disclosure, MPS is more stable either as a solid or in an non-aqueous formulation, and it is most active as an oxidizing agent (and tooth whitening agent) in an aqueous solution at pH 5-8. Accordingly, in some embodiments, the dispersant is non-aqueous and serves to stabilize the whitening agent in the oral care composition.

In one embodiment, the dispersant is non-aqueous, but the dispersant is sufficiently hydrophilic to react in an aqueous environment, such as the oral cavity, to release the whitening agent. The released whitening agent, such as MPS, will dissolve and activate in the aqueous environment. In other embodiments, the oral care composition is activated when exposed to water outside of the oral cavity.

In one embodiment, the oral care composition is non-aqueous, such that the moisture range of the oral care composition is about 5% or less.

In one embodiment, the dispersant is a poloxamer. In some embodiments, the dispersant is a liquid or paste like poloxamer, with average molecular weight less than 7000 Dalton. For example, the dispersant may include one or more of Pluronic® L35, Pluronic® L43, Pluronic® L64, Pluronic® L10, Pluronic® L44, Pluronic® L62, Pluronic® 10R5, Pluronic® 17R4, Pluronic® L25R4, Pluronic® P84, Pluronic® P65, Pluronic® P104, and Pluronic® P105. Pluronic® brand dispersants are commercially available from BASF, Florham Park, N.J.

In other embodiments, the oral care composition includes additional non-aqueous or suitable low water content dispersants in addition to a poloxamer. For example, in some embodiments, the oral care composition may include one or more of polyethylene glycols, such as PEG400 and PEG600, or polyethylene/polypropylene glycol copolymers, such as PEG/PPG 38/8 and PEG/PPG-116/66.

In one embodiment, the oral care composition includes from about 1% to about 99% non-aqueous dispersant based on the total weight of the oral care composition. In another embodiment, the oral care composition includes from about 10% to about 80% non-aqueous dispersant. In yet another embodiment, the oral care composition includes from about 20% to about 60% non-aqueous dispersant. For example, in one embodiment, the oral care composition includes from about 5% to about 99% L35, from about 10% to about 80% L35, or from about 20% to about 60% L35.

In various embodiments, the oral care composition may include more than one dispersants. For example, the oral care composition may include from about 5% to about 90% poloxamer; from about 0.1% to about 50% polyethylene glycol; and from about 0.1% to about 50% polyethylene/polypropylene glycol copolymers. In another embodiment, the oral care composition may include from about 10% to about 60% poloxamer; from about 1% to about 40% polyethylene glycol; and from about 1% to about 40% polyethylene/polypropylene glycol copolymers. In yet another embodiment, the oral care composition may include from about 15% to about 50% poloxamer; from about 2% to about 30% polyethylene glycol; and from about 2% to about 30% polyethylene/polypropylene glycol copolymers. For example, the oral care composition may include from about 15% to about 50% L35, from about 2% to about 30% PEG 600, and from about 2% to about 30% PEG/PPG-116/66.

Generally, viscosity is an important parameter for oral care compositions, such as toothpastes or whitening gels. For example, when the viscosity of an oral care composition is too low, it may become too runny and physical phase separation may take place. In some cases, this will not only affect the aesthetics of the oral care composition but also the homogeneity of the ingredients in the oral care composition. On the other hand, if the viscosity of the oral care compositions is too high, the oral care composition will be difficult to manufacture and package. In addition, oral care compositions with high viscosity are very difficult to evacuate from commonly used packages, such as tubes or syringes. Accordingly, it's important to select ingredients for oral care compositions that achieve a desirable range of viscosity to ensure product manufacturability, stability, and quality, as well as consumer acceptance.

In some embodiments, the viscosity of the oral care composition is from about 50,000 centipoise (cPs) to about 500,000 cPs at 25° C. In other embodiments, the viscosity of the oral care composition is from about 75,000 cPs to about 400,000 cPs at 25° C. In one embodiment, the viscosity of the oral care composition is from about 125,000 cPs to about 300000 cPs at 25° C.

In some embodiments, the oral care composition includes one or more structural builders.

As used herein, the term structural builder or structure building agent refers to a material that not only may thicken the oral care composition, but may also maintain the oral care composition in a homogenous state. That is, one where phase separation is minimized over time. While not bound by the theory, structure building agents typically interact with the dispersant via hydrogen bond and/or van der Waals interactions.

In some embodiments, the structural builder may be a polymer. In other embodiments, the structural builder is a cross-linked polymer, such as cross-linked polyvinylpyrrolidone ("PVP"). In one embodiment, the structural builder is a cross-linked polymer capable of interacting with the dispersant. For example, in some embodiments, cross-linked PVP swells in the presence of L35 by absorbing L35 into its cross-linked polymer network. Such interaction helps to prevent the solid (cross-linked PVP) from phase separating from the liquid (L35) in the oral care composition.

According to some embodiments, suitable structural builder polymers and co-polymers include N-vinyl lactam based polymers and copolymers. The monomers for preparing a vinyl lactam-based polymer or co-polymer of the present application includes any monomer having 3 to 8 atoms in a heterocyclic ring, comprising a carbonyl carbon atom and a heteroatom (such as N, S, O) in its vinyl moiety. Suitable monomers include but not limited to N-vinyl-2-pyrrolidone, N-vinyl-2-piperidone, N-vinyl-3-methyl-pyrrolidinone, N-vinyl-3-methyl-piperidone, N-vinyl-3-methyl-caprolactam, N-vinyl-4-methyl-pyrrolidinone, N-vinyl-4-methyl-2-pyrrolidone, N-vinyl-4-methyl-piperidone, N-vinyl-4-methyl-caprolactam, N-vinyl-5-methyl-pyrrolidinone, N-vinyl-5-ethyl-2-pyrrolidone, N-vinyl-4-methyl-piperidone, N-vinyl-3-ethyl-pyrrolidinone, N-vinyl-4,5-dimethyl-pyrrolidinone, N-vinyl-5,5-dimethyl-pyrrolidinone, N-vinyl-3,3,5-trimethyl-pyrrolidinone, N-vinyl-5-methyl-5-ethyl-pyrrolidinone, N-vinyl-3,4,5-trimethyl-3-ethyl-pyrrolidinone, N-vinyl-6-methyl-2-piperidone, N-vinyl-6-ethyl-2-piperidone, N-vinyl-3,5-dimethyl-2-piperidone, N-vinyl-4,4-dimethyl-2-piperidone, N-vinyl-2-caprolactam, N-vinyl-7-methyl-caprolactam, N-vinyl-7-ethyl-caprolactam, N-vinyl-3,5-dimethyl-caprolactam, N-vinyl-4,6-dimethyl-caprolactam, N-vinyl-3,5,7-trimethyl-caprolactam, N-vinyl-2-valerolactam, N-vinyl-hexahydro-2-azepinone, N-vinyl-octahydro-2-azocinone, N-vinyl octahydro-2-azoninone, and N-vinyl decahydro-2-azecinone.

The polymer may be a cross-linked polyvinylpyrrolidone, also known as poly-N-vinyl-poly-2-pyrrolidone, and commonly abbreviated to cross-linked "PVP." PVP generally refers to a polymer containing vinylpyrrolidone (also referred to as N-vinylpyrrolidone, N-vinyl-2-pyrrolidione and N-vinyl-2-pyrrolidinone) as a monomeric unit. The monomeric unit may include a polar imide group, four non-polar methylene groups, and a non-polar methane group. Cross linked PVP includes those commercially available as KOLLIDON® and LUVICROSS®, marketed by BASF, Mount Olive, N.J., USA; and POLYPLASDONE® INF-10, marketed by, Ashland, Covington, Ky., USA.

In one embodiment, the oral care composition includes from about 1% to about 60% structural builder based on the total weight of the oral care composition. In another embodiment, the oral care composition includes from about 5% to about 50% structural builder. In yet another embodiment, the oral care composition includes from about 10% to about 40% structural builder. For example, in one embodiment, the oral care composition includes from about 1% to about 60% PVP, from about 5% to about 50% PVP, or from about 10% to about 40% PVP. In one example, the oral care composition includes about 23% PVP based on the total weight of the oral care composition.

As described above, in some embodiments, the oral care composition may include additional ingredients common to oral care compositions, such as thickeners, flavoring agents, tartar control agents, surfactants, sweeteners, humectants, colorants, dyes, and pigments. In some embodiments, the oral care composition may include most orally acceptable additional ingredients common to oral care compositions. However, in some embodiment, the orally acceptable additional ingredient must be selected in view of the requirement to maintain a non-aqueous or a substantially non-aqueous oral care composition. For example, in some embodiments the additional ingredients will not affect the non-aqueous nature of the oral care composition.

In one embodiment, the oral care composition includes one or more surfactants. In some embodiments, the surfactants enhance stability of the composition, help clean the oral cavity surfaces through detergency, and provide foam upon agitation, e.g., during brushing with an oral care composition of the disclosure. Surfactants or surface active agents generally achieve increased whitening action by thoroughly dispersing the whitening agent throughout the oral cavity. In various embodiments, suitable surface active agents may function as a surface active agent, emulsifier, and/or foam modulator.

Any orally acceptable surfactant, most of which are anionic, nonionic, cationic, or amphoteric, can be used. A combination of surfactants may also be used. Suitable anionic surfactants include without limitation water-soluble salts of $C_{8-20}$ alkyl sulfates, sulfonated monoglycerides of $C_{8-20}$ fatty acids, sarcosinates, taurates and the like. Illustrative examples of these and other classes include sodium lauryl sulfate, sodium cocoyl monoglyceride sulfonate, sodium lauryl sarcosinate, sodium lauryl isoethionate, sodium laureth carboxylate, and sodium dodecyl benzenesulfonate. Suitable nonionic surfactants include without limitation poloxamers, polyoxyethylene sorbitan esters, fatty alcohol ethoxylates, alkylphenol ethoxylates, tertiary amine oxides, tertiary phosphine oxides, dialkyl sulfoxides and the like. Suitable amphoteric surfactants include, without limitation, derivatives of $C_{8-20}$ aliphatic secondary and tertiary amines having an anionic group such as carboxylate, sulfate, sulfonate, phosphate or phosphonate. A suitable example is cocoamidopropyl betaine.

In some embodiments, the oral care composition includes from about 0.01% to about 20.0% surfactant based on a total weight of the oral care composition. In other embodiments, the oral care composition includes from about 1.0% to about 10.0% surfactant. In one embodiment, the oral care composition includes about 2% surfactant based on a total weight of the oral care composition. For example, the oral care composition may include about 2% sodium lauryl sulfate.

In some embodiments, the oral care composition includes a thickening agent. Any orally acceptable thickening agent can be used, including without limitation carbomers, also known as carboxyvinyl polymers, carrageenans, also known as Irish moss and more particularly carrageenan (iota-carrageenan), high molecular weight polyethylene glycols (such as CARBOWAX™, available from The Dow Chemical Company), cellulosic polymers such as hydroxyethylcellulose, carboxymethylcellulose ("CMC") and salts thereof, e.g., CMC sodium, natural gums such as karaya, xanthan, gum arabic and tragacanth, colloidal magnesium aluminum silicate, and colloidal or fumed silica and mixtures of the same. The thickening agent may be a combination of one or more orally acceptable thickening agents.

In some embodiments, the oral care composition includes from about 0.1% to about 90% thickening agent based on a total weight of the oral care composition. In other embodiments, the oral care composition includes from about 0.2% to about 50% thickening agent. In yet another embodiment, the oral care composition includes from about 0.5% to about 35% thickening agent based on a total weight of the oral care composition. For example, the oral care composition may include about 2.3% fumed silica.

In some embodiments, the oral care composition includes an antioxidant. Acceptable antioxidants include BHA, BHT, vitamin A, carotenoids, vitamin E, flavonoids, polyphenols, ascorbic acid, herbal antioxidants, chlorophyll, melatonin and mixtures thereof. In some embodiments, the oral care composition includes from about 0.001% to about 1% antioxidants based on a total weight of the oral care composition. In one embodiment, the oral care composition includes about 0.03% antioxidant by weight.

According to one embodiment, the oral care composition includes one or more flavoring agent. Useful flavoring agents include any material or mixture of materials operable to enhance the taste of the oral care composition. Any orally acceptable natural or synthetic flavoring agent can be used, such as flavoring oils, flavoring aldehydes, esters, alcohols, similar materials, and combinations thereof. Flavoring agents include vanillin, sage, marjoram, parsley oil, spearmint oil, cinnamon oil, oil of wintergreen (methylsalicylate), peppermint oil, clove oil, bay oil, anise oil, eucalyptus oil, citrus oils, fruit oils and essences including those derived from lemon, orange, lime, grapefruit, apricot, banana, grape, apple, strawberry, cherry, pineapple, etc., bean- and nut-derived flavors such as coffee, cocoa, cola, peanut, almond, etc., adsorbed and encapsulated flavorants, and mixtures thereof. Also encompassed within flavoring agents herein are ingredients that provide fragrance and/or other sensory effect in the mouth, including cooling or warming effects. Such ingredients include menthol, menthyl acetate, menthyl lactate, camphor, eucalyptus oil, eucalyptol, anethole, eugenol, cassia, oxanone, x-irisone, propenyl guaiethol, thymol, linalool, benzaldehyde, cinnamaldehyde, N-ethyl-p-menthan-3-carboxamine, N,2,3-trimethyl-2-isopropylbutanamide, 3-1-menthoxypropane-1,2-diol, cinnamaldehyde glycerol acetal (CGA), methone glycerol acetal (MGA) and mixtures thereof.

In some embodiments, the oral care composition includes from about 0.01% to about 5% flavoring agents based on a total weight of the oral care composition. In another embodiment, the oral care composition includes from about 0.05% to about 2% flavoring agents. In yet another embodiment, the oral care composition includes from about 0.1% to about 3%, from about 0.2% to about 2.5%, or about 1.5% flavoring agents based on a total weight of the oral care composition. For example, the oral care composition may include about 1.5% of dental cream flavor.

In some embodiments, the oral care composition may also include one or more sweeteners. Sweeteners among those useful herein include orally acceptable natural or artificial, nutritive or non-nutritive sweeteners. Such sweeteners include dextrose, polydextrose, sucrose, maltose, dextrin, dried invert sugar, mannose, xylose, ribose, fructose, levulose, galactose, corn syrup (including high fructose corn syrup and corn syrup solids), partially hydrolyzed starch, hydrogenated starch hydrolysate, sorbitol, mannitol, xylitol, maltitol, isomalt, aspartame, neotame, saccharin and salts thereof, sucralose, dipeptide-based intense sweeteners, cyclamates, dihydrochalcones and mixtures thereof. Some embodiments may include one or more sweeteners. In some embodiments, the oral care composition includes from about 0.005% to about 5% sweeteners based on a total weight of the oral care composition. In other embodiments, the oral care composition includes from about 0.01% to about 1% sweeteners. For example, the oral care composition may include about 0.5% sodium saccharin and about 0.04% sucralose.

In some embodiments, the oral care composition may also include one or more pH modifying agents. PH modifying agents among those useful herein include acidifying agents to lower pH, basifying agents to raise pH and buffering agents to control pH within a desired range. For example, one or more compounds selected from acidifying, basifying and buffering agents can be included to provide a pH of 2 to 10, or in various embodiments from about 2 to about 8, from about 3 to about 9, from about 4 to about 8, from about 5 to about 7, from about 6 to about 10, and from about 7 to about 9. Any orally acceptable pH modifying agent can be used, including without limitation carboxylic, phosphoric and sulfonic acids, acid salts (e.g., monosodium citrate, disodium citrate, monosodium malate, etc.), alkali metal hydroxides such as sodium hydroxide, carbonates such as sodium carbonate, bicarbonates, sesquicarbonates, borates, silicates, phosphates (e.g., monosodium phosphate, trisodium phosphate, pyrophosphate salts, etc.), imidazole and mixtures thereof. One or more pH modifying agents are optionally present in a total amount effective to maintain the composition in an orally acceptable pH range. In some embodiments, the oral care composition includes from about 0.01% to about 10% pH modifier agents based on a total weight of the oral care composition. For example, the oral care composition may include about 0.9% sodium acid pyrophosphate (SAPP) and about 2% tetrasodium pyrophosphate (TSPP) as a pH modifier.

In some embodiments, the oral care composition may include colorants. Colorants, such as dyes or pigments, may be food color additives presently certified under the Food Drug & Cosmetic Act for use in food and ingested drugs, including dyes such as FD&C Red No. 3 (sodium salt of tetraiodofluorescein), Food Red 17, disodium salt of 6-hydroxy-5-{(2-methoxy-5-methyl-4-sulphophenyl)azo}-2-naphthalenesulfonic acid, Food Yellow 13, sodium salt of a mixture of the mono and disulphonic acids of quinophtalone or 2-(2-quinolyl) indanedione, FD&C Yellow No. 5 (sodium salt of 4-p-sulfophenylazo-1-p-sulfophenyl-5-hydroxypyrazole-3 carboxylic acid), FD&C Yellow No. 6 (sodium salt of p-sulfophenylazo-B-naphtol-6-monosulfonate), FD&C Green No. 3 (disodium salt of 4-{[4-(N-ethyl-p-sulfobenzylamino)-phenyl]-(4-hydroxy-2-sulfoniumphenyl)-methylene}-[1-(N-ethyl-N-p-sulfobenzyl)-DELTA-3,5-cyclohexadienimine], FD&C Blue No. 1 (disodium salt of dibenzyldiethyl-diamino-triphenylcarbinol trisulfonic acid anhydrite), FD&C Blue No. 2 (sodium salt of disulfonic acid of indigotin) and mixtures thereof in various proportions. Typically, colorants if included are present in very small quantities.

The oral compositions of the present disclosure may also include one or more other active ingredients, which are operable for the prevention or treatment of a condition or disorder of hard or soft tissue of the oral cavity, the prevention or treatment of a physiological disorder or condition, or to provide a cosmetic benefit.

Some embodiments of the present disclosure include a dental abrasive or combination of dental abrasive agents. As used herein, the term "abrasive" or "abrasive agent" also includes materials commonly referred to as "polishing agents." Any orally acceptable abrasive can be used, but typically, type, fineness (particle size) and amount of abrasive should be selected so that tooth enamel is not excessively abraded in normal use of the composition. Suitable abrasives include without limitation silica (in the form of silica gel, hydrated silica or precipitated silica), alumina, insoluble phosphates, calcium carbonate, resinous abrasives such as urea-formaldehyde condensation products and the like.

Among insoluble phosphates useful as abrasives are orthophosphates, polymetaphosphates and pyrophosphates. Illustrative examples are dicalcium orthophosphate dihydrate, calcium pyrophosphate, n-calcium pyrophosphate, tricalcium phosphate, calcium polymetaphosphate and insoluble sodium polymetaphosphate.

Average particle size of an abrasive, if present, is generally from about 0.1 to 100 about μm. For example, in one embodiment, the particle size is from about 1 to about 80 μm or from about 5 to about 60 μm. In some embodiments, one or more abrasives are present in an amount of from about 0.01% to about 70% by weight, based on the total weight of the oral care composition. In other embodiments, the oral care composition includes from about 0.1% to about 60% abrasives. In some embodiments, the abrasive is calcium pyrophosphate. In some embodiments, the oral care composition includes from 0.01% to about 70% calcium pyrophosphate based on a total weight of the oral care composition. In another embodiment, the oral care composition includes about 20% calcium pyrophosphate.

In various embodiments of the present disclosure, the oral care composition includes an anticalculus agent. Suitable anticalculus agents include without limitation phosphates and polyphosphates (for example pyrophosphates), polyaminopropanesulfonic acid (AMPS), hexametaphosphate salts, zinc citrate trihydrate, polypeptides, polyolefin sulfonates, polyolefin phosphates, diphosphonates. In some embodiments, the anticalculus agent is present in an amount of from about 0.01% to about 30% weight based on the total weight of the oral care composition. In some embodiments, the oral care composition includes a mixture of anticalculus agents. In some embodiments, tetrasodium pyrophosphate (TSPP) and sodium tripolyphosphate (STPP) are used as the anticalculus agents. In some embodiments, the anticalculus agent includes from 0.1% to 10% TSPP, or about 2% TSPP.

Another component of the present compositions may be a synthetic anionic polymeric polycarboxylate, which acts as a stabilizer for the polyphosphate anti-tartar agent and which may help to block access of painful or pain-causing materials, such as sugars, to the tooth nerves.

In some embodiments, the oral care composition optionally includes a source of fluoride ions. In some embodiments, the source of fluoride ions is selected from: fluoride, monofluorophosphate (MFP), and fluorosilicate salts. In some embodiments, one or more fluoride ion-releasing compounds are optionally present in an amount providing a total of 100 to 20,000 ppm, 200 to 5,000 ppm, or 500 to 2,500 ppm, fluoride ions. If present, in some embodiments, the amount of fluoride source in the oral care composition ranges from about 0.01% to about 10% by weight, based on the total weight of the oral care composition, typically about 1.1%. For example, in one embodiment, the oral care composition may include about 0.76% MFP.

The compositions also may include a stannous ion or a stannous ion source to mitigate calcium loss. Suitable stannous ion sources include without limitation stannous fluoride, other stannous halides such as stannous chloride dihydrate, stannous pyrophosphate, organic stannous carboxylate salts such as stannous formate, acetate, gluconate, lactate, tartrate, oxalate, malonate and citrate, stannous ethylene glyoxide and the like. In some embodiments, one or more stannous ion sources are included in the oral care composition. For example, the oral care composition may include from about 0.01% to about 10% stannous ion source by weight, based on the total weight of the oral care composition. In one embodiment, the oral care composition includes from about 0.1% to about 7% stannous ion source or from about 0.2% to about 5% stannous ion source.

EXAMPLES

Aspects of the present disclosure may be further understood by referring to the following examples. The examples are illustrative, and are not intended to be limiting embodiments thereof. Table 1 illustrates an oral care composition according to an embodiment of the present disclosure. Example 1 illustrates an embodiment of a process to make the oral care composition of Table 1.

TABLE 1

| Oral Care Composition #1 | |
|---|---|
| Ingredient | Weight % |
| Oxone ® | 1% (0.5% MPS) |
| Insoluble Phosphate Abrasive | 15% |
| Polyvinyl Pyrrolidone (PVP) | 23% |
| Thickening Agent | 2.3% |
| Flavoring Agents and Sweeteners | 2.04% |
| pH Modifying Agents | 2.9% |
| Sodium Monofluorophosphate (MFP) | 0.76% |
| Polyoxyethylene-Polyoxypropylene Glycol (L35) | 36% |
| Polyethylene Glycol 600 (PEG 600) | 10% |
| Polyethylene Glycol/Polypropylene Glycol 116/66 Copolymer | 5% |
| Sodium Lauryl Sulfate Powder (SLS) | 2% |
| Total Components | 100% |

Example 1

An oral care composition including the ingredients listed in Table 1 was prepared as follows: The formula amount of L35 and the other non-aqueous or low water dispersants were added to a Ross mixer and mixed on high speed for 2 minutes with no vacuum. The Formula amounts of PVP and the thickening agent were then added to the Ross mixer. The powders were wetted, and the resulting mixture was mixed at maximum speed for 2 minutes under full vacuum. The formula amounts of the dental abrasives, pH modifying agents, anticalculus agents, fluoride ion source, and sweeteners were added to the Ross mixer. The powders were wetted, and the resulting mixture was mixed at maximum speed for 2 minutes under full vacuum. The formula amounts of the surfactants and MPS were then added to the Ross mixer and the resulting mixture was mixed at medium speed for 5 minutes under vacuum. Finally, the formula amount of the flavoring agents were added, and the mixture was mixed on medium speed with no vacuum, and then for 10 minutes under full vacuum.

The potential effectiveness of tooth whitening oral care compositions can be measured in terms of active oxygen content. For example, the term active oxygen can be correlated with the amount of peroxide present in the composition. One of the oxygen in each peroxide group is considered "active". The percentage of active oxygen (AO) in a given composition can be defined by the following Formula 1:

$$[AO] \% = \text{Equivalent of AO} * MW \text{ of AO/Weight of sample} \quad \text{Formula 1}$$

In one embodiment, the stability of the oral care composition can be determined by monitoring the change of active oxygen level over time. The level of active oxygen can be obtained experimentally by a well-known thiosulfate based titration method. This method is also commonly used to determine the active oxygen level in hydrogen peroxide containing compositions as well.

The amount of active oxygen in the oral care composition of Table 1 was determined via this active oxygen titration method as follows: about 1.3 grams of the Table 1 composition was added to a beaker. 25 ml of glacial acetic acid was then added, followed by addition of 50 ml of ethanol/water (1:1 volume ratio "v/v"). The mixture was then mixed until the Table 1 composition was fully suspended. 5 ml of 20% (by weight) potassium iodide solution and 4 drops of ammonium molybdate solution were added to the mixture and mixed for 5 minutes. The mixture turned yellowish. 2 ml of a starch indicator was added to the mixture. The mixture turned dark brown in color. The mixture was then titrated with 0.1 N sodium thiosulfate solution until the dark color disappeared and the amount (mL) of sodium thiosulfate solution used was recorded. The percentage of active oxygen (% AO) was then calculated as follows:

$$(\% \ AO) = \frac{(\text{ml thiosulfate used}) \times (N \text{ of thiosulfate}) \times (\text{meq wt of oxidizing agent}) \times (100)}{\text{weight of sample (g)}} \quad \text{Formula 2}$$

where the meq wt of the oxidizing agent is 0.008

To determine the stability of the oral care composition, the % AO was measured before aging and after aging at 40° C. as illustrated in Table 2. The oral care composition was aged up to 13 weeks, which is the extent of time commonly used to predict a 24 month shelf life under normal conditions. Under normal conditions, maintenance of about 70% or more of the initial % AO after 8 weeks is considered a good result, and signifies that the composition will be sufficiently stable for commercial distribution and sales, and maintenance of about 70% or more of the initial % AO after 13 weeks is considered a surprisingly good result.

TABLE 2

| | AO % | | | |
|---|---|---|---|---|
| | Initial | After 4 weeks | After 8 weeks | After 13 weeks |
| Oral Care Composition #1 | 0.057% | 0.049% | 0.047% | 0.044% |

As illustrated in Table 2, the oral care composition had an initial drop of % AO of about 20% and then remained relatively stable during the rest of the 13-week accelerated aging study. This result indicates a very good stability. As a comparison, an unstable oral care composition (Oral Care Composition #2 in Table 3) that contains the similar starting concentration of Oxone showed much more active oxygen loss under similar aging conditions (Table 4).

TABLE 3

Comparative Oral Care Composition #2

| Ingredient | Weight % |
|---|---|
| Oxone ® | 1% (0.5% MPS) |
| Insoluble Phosphate Abrasive | 20% |
| Polyvinyl Pyrrolidone (PVP) | 5.75% |
| Thickening Agent | 1.75% |
| Flavoring Agents and Sweeteners | 1.98% |
| pH Modifying Agents | 2% |
| Butylated hydroxytoluene | 0.03% |
| Sodium Monofluorophosphate (MFP) | 1.1% |
| Phosphoric acid (85%) | 0.2% |
| Glycerin | 34.43 |
| Propylene glycol | 15.95 |
| Polyethylene Glycol 600 (PEG 600) | 6.31% |
| Polyethylene Glycol/Polypropylene Glycol 116/66 Copolymer | 7.5% |
| Sodium Lauryl Sulfate Powder (SLS) | 2% |
| Total Components | 100% |

TABLE 4

| | AO % | | | | |
|---|---|---|---|---|---|
| | Theoretical | Initial | After 2 weeks | After 4 weeks | After 8 weeks |
| Oral Care Composition #2 | 0.052% | 0.036% | 0.017% | 0.016% | 0.016% |

As described above, in some embodiments, the oral care composition is non-aqueous. In addition, in some other embodiments, the oral care composition should be substantially free of liquid ingredients with a high density of hydroxyl groups, such as polyol-type humectants including glycerin, sorbitol, propylene glycol, or compounds with similar structural features. While not bound by the theory, it is believed that ingredients with a high density of hydroxyl groups have a strong tendency to absorb moisture. Because peroxysulfuric acid salts, such as MPS, are moisture sensitive, excess moisture accumulation in the oral care composition will activate the MPS during storage, and lead to greater active oxygen loss. In addition, the hydroxyl groups in these ingredients may also directly react with the whitening agent, and therefore further reduce the stability of an oral care composition. These effects are illustrated in Tables 3-4. As illustrated in Tables 1 and 3, Oral Care Composition #1 includes a non-aqueous dispersant (L35), whereas Oral Care Composition #2 includes glycerin and propylene glycol. As illustrated in Tables 2 and 4, Oral Care Composition #1 displays much greater stability during storage than Oral Care Composition #2.

In some embodiments, the oral care compositions disclosed herein have a whitening efficiency which is greater than a whitening efficiency of a commercial available whitening toothpaste. As used herein, the phrase "whitening efficacy" is intended to refer to the amount of change in tooth color. The color change can be measured according to the L*a*b* color scale. The luminance or lightness (L*) value measures brightness and varies from a value of one hundred for perfect white to zero for black, assuming a* and b* are zero. The a* value is a measure of redness when positive, gray when zero and greenness when negative. The b* value is a measure of yellowness when positive, gray when zero and blueness when negative. Generally, teeth appear whiter as: the L* value increases meaning they become brighter, the a* value increases or decreases, depending upon whether the stained teeth have a green tint or red tint prior to whitening, and the b* value decreases meaning they become less yellow. While this is the general relationship for perceived whitening, the b* value might also slightly increase if the magnitude of the increase of the L* value is large enough. Similarly, the L* value might also decrease if the magnitude of the decrease of the b* value is large enough to overshadow the less significant change in L*.

In some embodiments, the whitening index (W*) is used to assess tooth whiteness. The whiteness index is based on the distance of a color value from a nominal white point, represented in CIELAB color space as L*=100, a*=0 and b*=0, and defined according to the following formula 3:

$$W^* = [(a^*)^2 + (b^*)^2 + (L^* - 100)^2]^{1/2}. \quad \text{Formula 3}$$

Changes in W* may be used to assess the whitening efficacy of a composition before and after a treatment. The following Formula 4 may be used to calculate ΔW*:

$$\Delta W^* = W^*(\text{Treatment}) - W^*(\text{baseline}). \quad \text{Formula 4}$$

Other values which may be used to assess tooth whiteness are described in Joiner et al., "A Review of Tooth Colour and Whiteness", *Journal of Dentistry*, 2008, 36S:S2-S7, herein incorporated by reference in its entirety.

The whitening efficacy of oral care compositions according to embodiments of this disclosure was tested using in vitro brushing studies as follows: artificially stained bovine central incisors mounted in a resin were purchased from Dental Product Testing Therametric Technologies, Inc. Only teeth with L* values above 58 and below 64 were selected. Two slurries were used to brush the bovine incisors for 2 minutes under a 250 g force. One slurry contained 2 g of oral composition #1 and 2 g of artificial saliva. The other slurry contained 2 g of a commercial whitening toothpaste and 2 g of artificial saliva. L, a, b values were measured using a SPECTROSHADE Micro instrument manufactured by Medical High Technology (MHT). The teeth were treated for 14 brushing cycles to mimic 7 days (day & night) brushing routine. The results of the brushing study are illustrated in Table 5 and FIG. 1. The lower the ΔW value, the whiter the tooth.

TABLE 5

|  |  | Number of Brushing Treatments |  |  |  |  |  |  |  |
|---|---|---|---|---|---|---|---|---|---|
|  |  | 0 | 2 | 4 | 6 | 8 | 10 | 12 | 14 |
| Oral Care Composition #1 (initial) | ΔW | 0 | −2.71 | −3.89 | −4.23 | −5.36 | −5.50 | −6.10 | −7.14 |
|  | Std. Dev. | 0 | 1.23 | 0.54 | 1.27 | 1.80 | 1.69 | 1.59 | 2.18 |
| Oral Care Composition #1 (13 weeks aged) | ΔW | 0 | −2.43 | −3.67 | −4.46 | −5.18 | −6.03 | −6.28 | −6.75 |
|  | Std. Dev. | 0 | 0.71 | 1.10 | 1.35 | 1.46 | 1.81 | 1.80 | 1.94 |
| Commercial Whitening Toothpaste | ΔW | 0 | −0.95 | −2.22 | −1.88 | −1.87 | −2.167 | −2.387 | −2.727 |
|  | Std. Dev. | 0 | 1.247 | 1.12 | 1.86 | 1.11 | 1.27 | 1.44 | 1.86 |

The commercial whitening toothpaste used for Table 5 used a hydrogen peroxide whitening agent. In particular, the commercial whitening toothpaste uses 0.55% cross-linked PVP/hydrogen peroxide complex as the whitening agent, based on a total weight of the commercial whitening toothpaste. In particular, the commercial whitening toothpaste used 0.55% cross-linked PVP/hydrogen peroxide complex as the whitening agent, based on a total weight of the commercial whitening toothpaste, for a 0.1% HP content.

Figure 1:
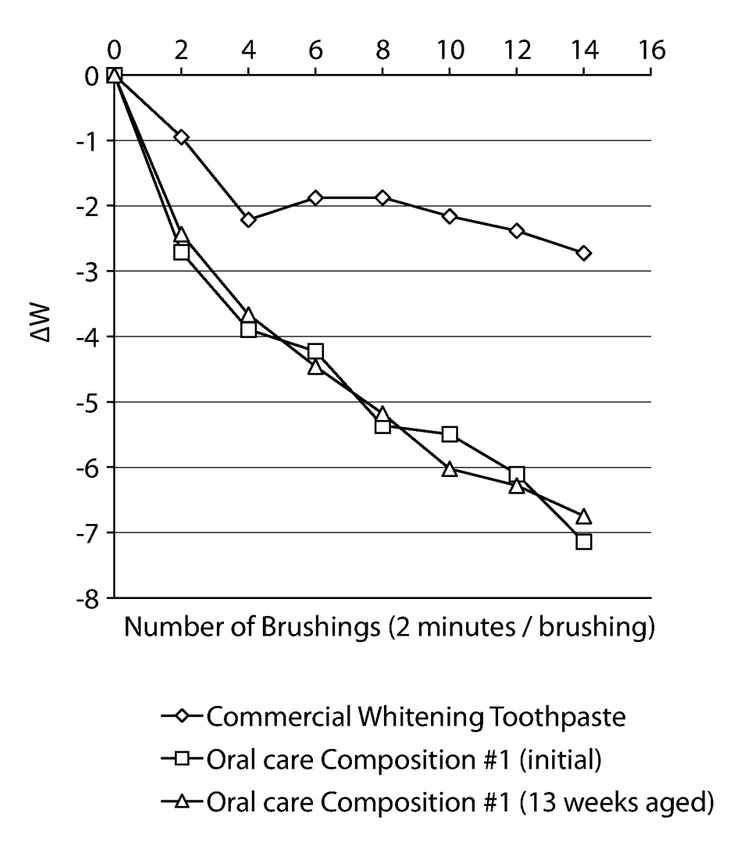
FIG. 1 is a graph illustrated a whitening efficacy of an oral care composition according to an embodiment.

As illustrated in Table 5 and FIG. 1, teeth brushed using oral care composition #1 had a lower ΔW value when compared to teeth brushed using a commercial whitening toothpaste. Table 5 and FIG. 1 demonstrate the superior whitening efficacy of oral care composition according to embodiments of the present disclosure. The results also indicate the stability of oral care composition #1. After 13 weeks of accelerated aging at 40 C, oral care composition #1 had the same whitening performance as when it was freshly made.

In some embodiments, the present disclosure provides methods to whiten an oral surface in a human or animal subject. The method may include contacting a tooth surface with an oral care composition according to embodiments of the present disclosure. As used herein "animal subject" includes non-human mammals, such as canines, felines and horses. In one embodiment, the oral care composition is contacted with an oral surface of the mammalian subject to thereby whiten teeth in a highly efficacious manner.

In various embodiments, the oral care composition prepared in accordance with the present disclosure may be applied regularly to an oral surface, for example on a daily basis, at least one time daily for multiple days, or alternately every second or third day. In some embodiments, the oral care composition is applied to the oral surfaces from 1 to 3 times daily, for at least 2 weeks up to 8 weeks, from four months to three years, or more up to a lifetime.

In some embodiments, the oral care composition may be embodied as a gel and may be applied directly to the teeth using a delivery device, such as a pen, a liquid stick having an applicator, such as a felt tip, brush, roller ball, or non-woven pad, in an amount sufficient to effect whitening once activated. In some embodiments, the oral care composition is activated once exposed to the aqueous environment of the oral cavity or when exposed directly to water or saliva. In some embodiments, the oral care composition of the present disclosure is maintained on the surface of the tooth for a plurality of minutes.

In some embodiments, the oral care composition is activated and maintained on the surface of a tooth for from about 1 minute to about 8 hours. In some embodiments, the composition is activated and maintained on the surface of a tooth for from about 5 minutes to about 4 hours. In some embodiments, the composition is activated and maintained on the surface of a tooth for from about 10 minutes to about 120 minutes. In some embodiments, the composition is activated and maintained on the surface of a tooth for about 15 minutes to about 60 minutes. In some embodiments, the composition is activated and maintained on the surface of a tooth for from about 20 minutes to about 45 minutes.

The present disclosure has been described with reference to exemplary embodiments. Although a limited number of embodiments have been shown and described, it will be appreciated by those skilled in the art that changes may be made in these embodiments without departing from the principles and spirit of preceding detailed description. It is intended that the present disclosure be construed as including all such modifications and alterations insofar as they come within the scope of the appended claims or the equivalents thereof.

What is claimed is:

1. An oral care composition, wherein all ingredients are orally acceptable, and the oral care composition comprises:
   0.5% potassium peroxymonosulfate;
   23% PVP;
   36% of liquid poloxamer, and
   5% of polyethylene/polypropylene glycol copolymer which is PEG/PPG 116/66;
   wherein the PVP is cross-linked polyvinylpyrrolidone, and
   wherein the moisture range of the oral care composition is 5% or less.

2. The oral care composition of claim 1, wherein the oral care composition does not include a hydrogen peroxide compound.

3. The oral care composition of claim 1, wherein the composition is a toothpaste or whitening gel.

4. The oral care composition of claim 1, wherein a viscosity of the oral care composition is from about 50000 to about 500000 cPs.

5. The oral care composition of claim 1, wherein an active oxygen content of the oral care composition is greater than about 70% of an initial active oxygen content of the oral care composition after 8 weeks of aging at 40° C.

6. The oral care composition of claim 1, wherein an active oxygen content of the oral care composition is greater than about 70% of an initial active oxygen content of the oral care composition after 13 weeks of aging at 40° C.

7. The oral care composition of claim 1, further comprising at least one of a surfactant, a thickening agent, an antioxidant, a flavoring, a sweetener, a pH modifiers, an abrasive, an anticalculus agent, a source of fluoride ions, a stannous ion source, a colorant, and a dye or pigment.

8. A method of whitening a tooth surface, comprising:
   applying an oral care composition according to claim 1 to the tooth surface; and
   activating the oral care composition by exposing the oral care composition to water or saliva.

9. The method of claim 8, wherein a viscosity of the oral care composition is from about 50,000 cPs to about 500,000 cPs.

* * * * *